United States Patent [19]

Christensen

[11] Plant 5,035

[45] Apr. 12, 1983

[54] HYBRID MINIATURE ROSE PLANT CV. ARORASP

[75] Inventor: Jack E. Christensen, Ontario, Calif.

[73] Assignee: Armstrong Nurseries, Inc., Ontario, Calif.

[21] Appl. No.: 314,239

[22] Filed: Oct. 23, 1981

[51] Int. Cl.[3] ..... A01H 5/00

[52] U.S. Cl. ..... Plt./8

[58] Field of Search ..... Plt./8

*Primary Examiner*—Robert E. Bagwill

*Attorney, Agent, or Firm*—Synnestvedt & Lechner

[57] ABSTRACT

A miniature rose having yellow blossoms with wavy petals.

1 Drawing Figure

1

This invention relates to a hybrid miniature rose plant (ARORASP) of the half-hardy dwarf type. The plant is a bush outdoor seedling cultivated primarily for cut flowers and garden decoration.

The seed parent was "Gingersnap" (U.S. Plant Pat. No. 4,330) and the pollen parent "Magic Carrousel" (U.S. Plant Pat. No. 3,601). The plant was first propagated in Ontario, Calif., and the descriptive and comparative reference to this plant and its bloom hereinafter will relate to plants of the same class grown in this region. This variety preserves its distinguishing characteristics through succeeding propagations, by cuttings and budding.

This new variety is most readily distinguished from its seed parent, Gingersnap, by the combination of the following characteristics. Whereas Gingersnap bears flowers of a relatively uniform bright orange coloration, the new rose Arorasp bears flowers of a uniform deep yellow coloration essentially as described and illustrated herein. Gingersnap is classified as a hybrid floribunda, whereas the new cultivar Arorasp falls into the hybrid miniature class. The new rose Arorasp has significantly fewer petals (12 to 18) than does Gingersnap (25 to 36).

The new variety differs from its pollen parent, Magic Carrousel, most notably in the following respects. Magic Carrousel produces flowers of a white and red coloration whereas the new cultivar Arorasp bears deep yellow flowers, essentially as described and illustrated herein. Whereas the new rose Arorasp bears flowers of 12 to 18 petals, Magic Carrousel bears flowers of significantly higher petalage (24 to 30 as described in Modern Roses VIII published by the American Rose Society; however, an examination of Magic Carrousel roses growing mid-summer in Ontario, Calif. the flowers had 30 to 40 petals). Magic Carrousel bears styles of white and pink coloration whereas the new cultivar Arorasp bears deep red styles.

The flowers are usually borne singly, but sometimes two or more to a stem in irregular clusters on strong stems, long for miniature roses. The plant blooms abundantly outdoors, and nearly continuously during the growing season. The blooms have a slight tea fragrance.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values

2 based upon The R.H.S. Colour Chart, put out by The Royal Horticultural Society in London.

BUD

The peduncle is of an average length for miniature roses, is of average caliper, erect and moderately smooth and has numerous stipitate glands. The color is between Yellow Green 144A and Green 143C sometimes with a light blush near Red 46A.

Before the calyx breaks, the bud is medium to large in size for miniature roses and of medium to long length, pointed and ovoid, with foliaceous appendages and a few stipitate glands on the surface of the bud. Usually, slender, much cut, foliaceous parts extend beyond the tip of the bud one-quarter or more of its length.

As the calyx breaks, the color is between Yellow-Orange 14A and Yellow-Orange 15B. The inner surface of the sepals carries a fine wooley tomentum and the margins are lined with stipitate glands.

As the first petal opens, the bud is of average to large size for miniature roses and of long, pointed and ovoid form. The color on the outside and inside of the petal is between Yellow-Orange 17B and Yellow-Orange 15B. The bud opens up well, and is not prevented from opening by cold, hot, wet or dry weather.

BLOOM

The size of the bloom when fully open is average to large for miniature roses, being from 1" to 1½" in diameter. Petalage is double, with from 12 to 18 petals, plus 0 to 4 petaloids arranged regularly. The bloom is cupped to high-centered at first, becoming open to cupped. At first the petals remain somewhat tightly cupped, with tips reflexed slightly outward; later at maturity the petals become very cupped.

PETALS

The petals are thick in texture and slightly satiny both inside and outside. The outside petals are broadly obovate with a pointed apex. Intermediate petals are round to obovate with a pointed apex. The inside petals are obovate with an irregular apex.

The paragraph immediately following describes color values observed in a flower newly opened in the month of August. The plant had been grown outdoors, in Ontario, Calif.

The outside and inside surfaces of all petals (outside, intermediate and inner) were all essentially the same in coloration, being between Yellow-Orange 14B and Yellow 13A with a small basal attachment zone of near Yellow 10A.

The following paragraph describes color values observed in a flower which had been open for three days in the month of August. The plant had been grown outdoors in Ontario, Calif.

The outside and inside surfaces of both the outer and the inner petals were between Yellow 13B and Yellow-Orange 14C.

The general color effect of the newly opened flower is uniform and between Yellow-Orange 14B and Yellow 13A. The color effect was uniform and between Yellow 13B and Yellow-Orange 14C in a flower that had been three days open. The petals persist, fading to near Yellow 10A. The flower is not particularly affected by cold, hot, wet or dry weather.

The flower on the bush in the garden persists for from 3 to 5 days in the month of October. Cut roses grown outdoors and kept at living-room temperatures persist for from 4 to 6 days in the month of August.

REPRODUCTIVE ORGANS

The stamens are average to many in number for miniature roses and are arranged regularly about pistils.

The filaments are medium to long in length, and near Yellow-Orange 14B in color. Most are with anthers.

The anthers are medium to large in size for miniature roses, all opening at about the same time. Their color when immature is near Yellow-Orange 15C and when mature near Greyed-Orange 165A.

There is an abundant amount of pollen which is near Yellow-Orange 14B in color.

The pistils are approximately 25 in number, this being average.

The styles are moderately uneven, short to average in length, of heavy caliper, and somewhat loosely bunched; in color the styles are near Red 46A.

The stigma is near Red 46A in color.

The ovaries are usually all enclosed in the calyx.

The hips are globular and of average length. At maturity, they are near Orange 25B in color and have moderately smooth, thick, fleshy walls.

The sepals fall soon, are of medium to long length and spear-shaped. The color on the inside of the sepals is near Greyed-Orange 174A and near Yellow-Green 144C on the outside.

There are from 2 to 15 seeds of medium size, that is, from an average number to many seeds for miniature roses.

FOLIAGE

The compound leaves usually comprise 3 to 7 leaflets. They are abundant, of medium to large size for miniature roses, heavy to somewhat leathery, and semi-glossy. The leaflets are ovate with mucronate apex, round base and simply serrate margins.

The upper surface of the mature foliage is between Green 136A and Green 137A in color. The under surface is near Yellow Green 147B.

The young foliage is between Greyed-Purple 183A and Greyed-Purple 183B on its upper and under surfaces.

The rachis is average in size, grooved on its upper side with a few stipitate glands on the edges. The under side is sparsely prickly and has stipitate glands.

The stipules are medium to long in length, of medium width, with medium-length points turning out at an angle of more than 90°. Stipule edges are lined with numerous stipitate glands.

The plant displays a more than average resistance to mildew and blackspot when compared to other commercialized varieties grown under comparable conditions in Ontario, Calif.

GROWTH

The plant is a dwarf variety having a bushy, upright and much branched habit. Its growth is very vigorous, with canes which are of medium to heavy caliper for miniature roses.

The main stems are near Yellow Green 147B in color. They bear few large prickles which are medium to long length, almost straight with a moderately long narrow base. There are a few small prickles and no hairs. The large and small prickles are near Greyed-Orange 165B in color.

The branches are between Yellow-Green 146D and Green 143A in color. They bear a few large prickles from medium to long length, almost straight, with a moderately long broad base. These large prickles are near Greyed Orange 165B in color. There are very few small prickles and no hairs; the small prickles are near Greyed-Orange 165B.

New shoots are between Greyed-Orange 176A and Greyed-Red 178A in color. They bear a few large prickles which are of medium to long length, almost straight, with a moderately long broad base. The color of these large prickles is near Greyed Red 181A. There are a few prickles and no hairs. The small prickles are near Greyed-Red 181A in color.

I claim:

1. A new and distinct variety of rose plant of the hybrid miniature class, substantially as herein shown and described, and being especially characterized by its deep yellow buds and blooms of unique wavy form, by its tall, vigorous, upright, bushy habit that produces, on long stems suitable for cutting, flowers of heavy substance and good color retention.

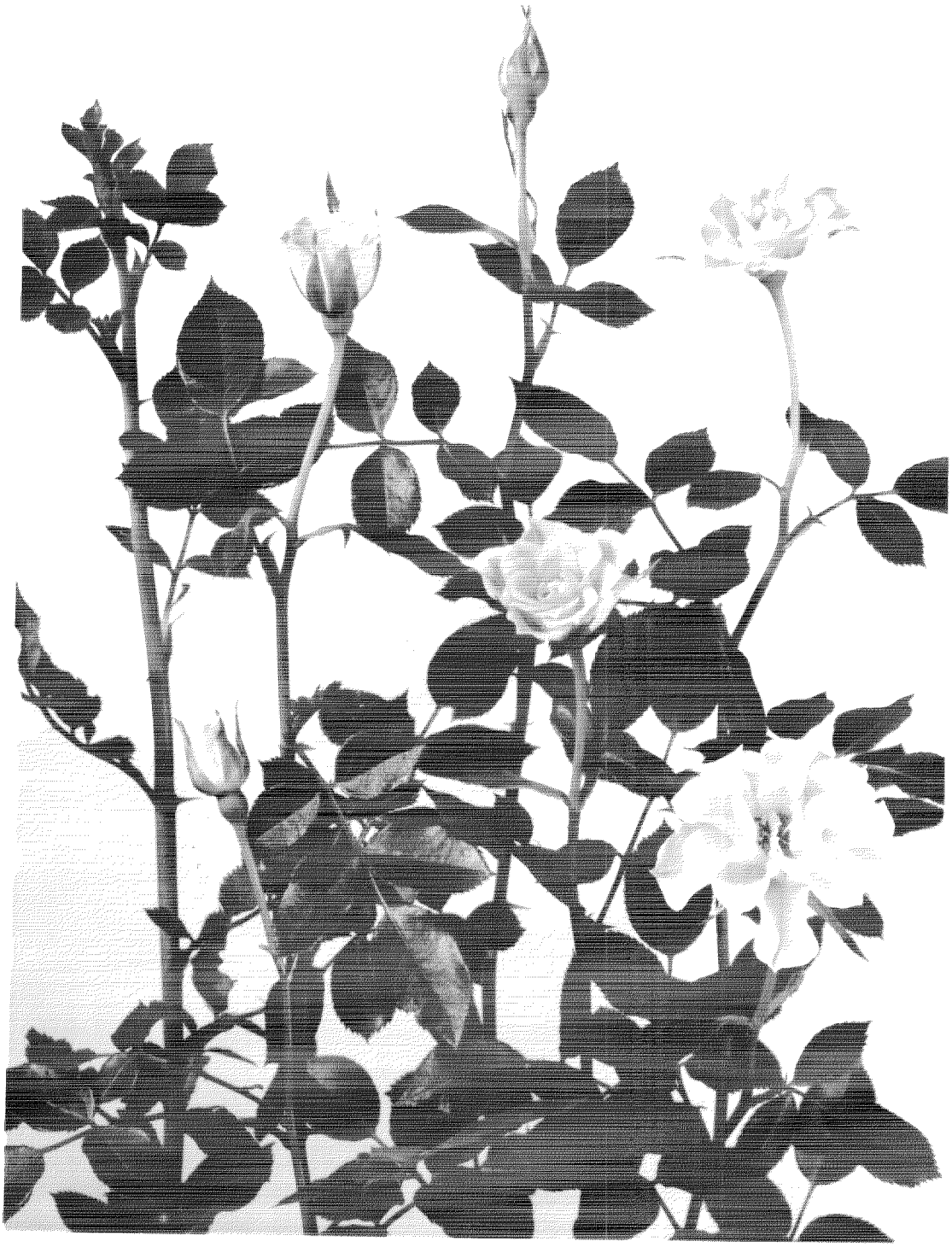

* * * * *